United States Patent
Ge et al.

(10) Patent No.: US 8,043,637 B2
(45) Date of Patent: Oct. 25, 2011

(54) COMBINATIONS OF HERB EXTRACTS HAVING SYNERGISTIC ANTIOXIDANT EFFECT, AND METHODS RELATING THERETO

(75) Inventors: Haiyan Ge, Scottsdale, AZ (US); Earl P. Seitz, Jr., Scottsdale, AZ (US); Thomas Doering, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 67 days.

(21) Appl. No.: 12/484,841

(22) Filed: Jun. 15, 2009

(65) Prior Publication Data

US 2010/0316747 A1    Dec. 16, 2010

(51) Int. Cl.
*A61K 36/35* (2006.01)
*A61K 36/00* (2006.01)
*A61K 36/355* (2006.01)
*A61K 36/906* (2006.01)

(52) U.S. Cl. ........................................ 424/756; 424/725
(58) Field of Classification Search ........................ None
See application file for complete search history.

(56) References Cited

U.S. PATENT DOCUMENTS

| 6,027,728 | A | 2/2000 | Yuen |
| 6,264,995 | B1 | 7/2001 | Newmark et al. |
| 6,576,286 | B1 | 6/2003 | Chen |
| 2003/0007939 | A1* | 1/2003 | Murad .......................... 424/61 |
| 2007/0077343 | A1 | 4/2007 | Ma et al. |
| 2007/0154575 | A1 | 7/2007 | Shimoda et al. |

FOREIGN PATENT DOCUMENTS

| JP | 2002047133 A | * | 2/2002 |
| WO | WO 2007/042472 A1 | | 4/2007 |

OTHER PUBLICATIONS

PCT International Search Report (PCT/US2010/037886) dated Mar. 1, 2011.

* cited by examiner

*Primary Examiner* — Qiuwen Mi
(74) *Attorney, Agent, or Firm* — Frank T. Barber

(57) ABSTRACT

The present invention comprises mixtures of herb extracts which exert synergistic antioxidant effect and comprise the herb ginger and at least one other herb selected from the group consisting of honeysuckle and *sophora*. Skin care preparations incorporating such herb extract mixtures, and their methods of preparation and use, are also claimed.

8 Claims, 2 Drawing Sheets

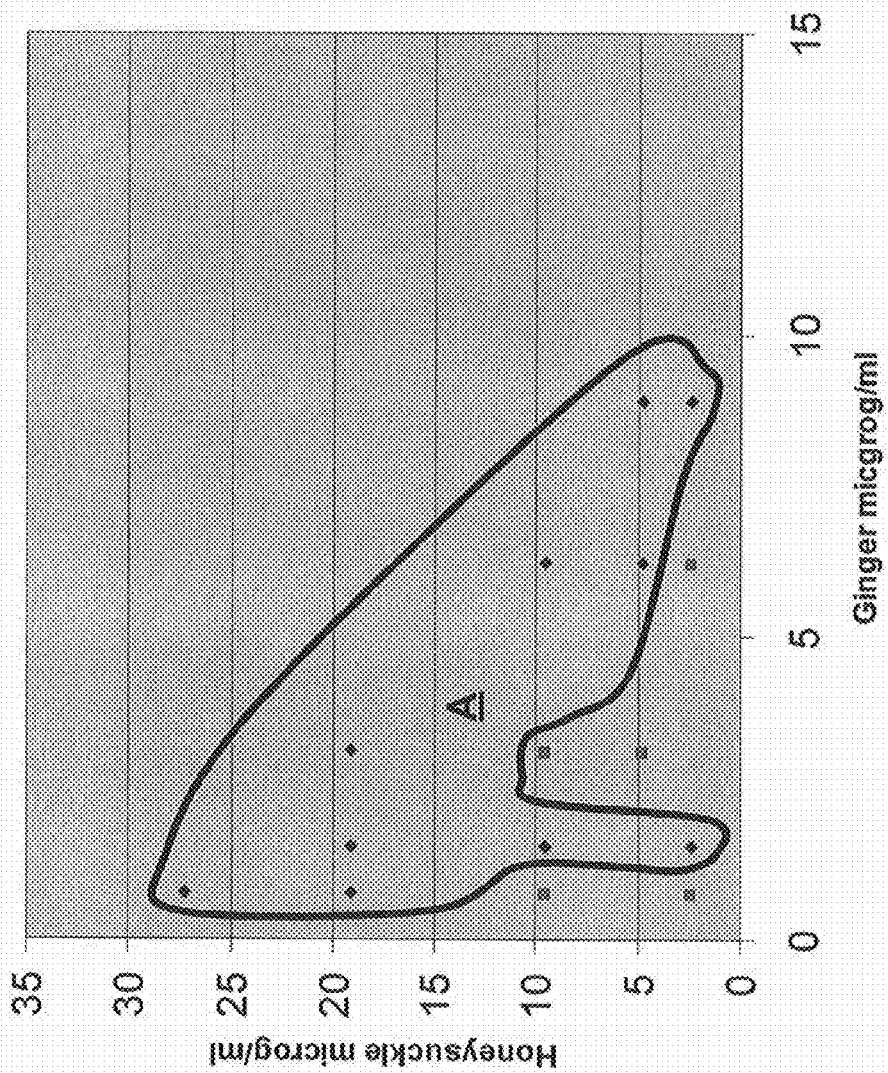

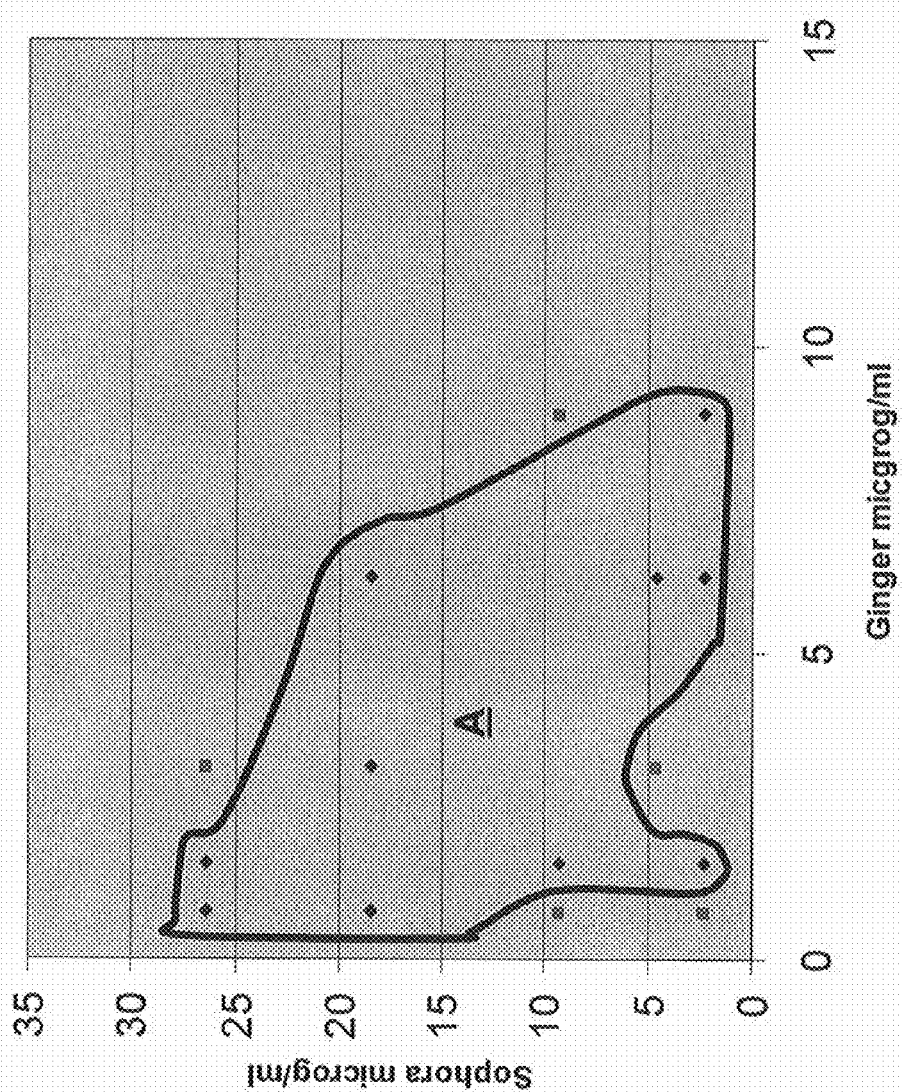

COMBINATIONS OF HERB EXTRACTS HAVING SYNERGISTIC ANTIOXIDANT EFFECT, AND METHODS RELATING THERETO

FIELD OF THE INVENTION

The present invention relates to combinations of herb extracts which provide synergistic antioxidant effects when used in personal care products including body washes, lotions, liquid hand soaps, sunscreens, shampoos, and the like. The invention also relates to the methods for preparing skin care preparations incorporating such combinations of herb extracts, as well as the methods for caring for the skin utilizing such preparations.

BACKGROUND

The use of various antioxidant compositions for counteracting the deleterious effect of free radicals upon cells of the human body is widely studied. Free radicals are implicated in a wide variety of diseases of the human body. Referring particularly to diseases of the skin, the presence of free radicals on the skin results from a number of conditions, including over-production of free radicals within the cell itself, or exposure to external forces such as ultraviolet rays, coupled with an inability of the cell itself to defend against the overproduction. The resulting excess of free radicals is known to be the cause of various skin disabilities, such as wrinkling, lack of elasticity, and generalized aging, and there is a need to fortify and supplement the various antioxidant mechanisms in the body.

Many compositions have been proposed and used in the past for providing the desired antioxidant effect, including Vitamin E (tocopherol), Vitamin A (beta-carotene), Vitamin C (ascorbic acid), Trolox (a Vitamin E analog), and the like. In addition, certain plant extracts have been reported as having antioxidant properties, including extracts from birch *Betula platyphylla*) (JP-A-10-046143) and various plant extracts obtained by extraction, with water or a lower alcohol or an aqueous lower alcohol solution, of plants such as *hibiscus, aloe*, rhubarb, osei (polygonati rhizoma), bearberry leaf, enmeiso (plectranthi herba), yobaihi (nyricae cirtex), *pueraria* root, *cnidium* rhizome, *atractylodes lancea* rhizome, *mentha* leaf, *glycyrriliza*, peony root, *coix* seed, sin'i (magnoliae flos), cinnamon bark, *houttuynia* herb, *coptis* rhizome, moutan bark, gentian, nutgall, *swertia* herb, *geranium* herb, *phellodendron* bark, dried ginger, *scutellaria* root, chulling (poly porus), garlic, sage, oregano, rosemary, laurel, celery, thyme, tarragon, nutmeg, mace, clove, Japanese horseradish, savory, basil, red pepper, roasted bean, black tea, green tea, persimmon leaf, coffee, horsetail, henon bamboo, mugwort, *Cynostemma* species, low striped bamboo, matrimony vine, *Cyrtomium* species, and shiitake mushrooms (JP-A6-024937). [See US published patent application Publication No. 2004/0028643].

Personal care products such as body washes, lotions, liquid hand soaps, sunscreens, shampoos, and the like ordinarily contain a variety of additives designed to provide performance enhancing benefits such as moisturizing, fragrance, colorant, anti-inflammatory, and anti-irritant properties, and thus these personal care products provide a convenient vehicle for also applying antioxidants directly to the skin. Botanical extracts are a source for many of the above performance enhancing properties and accordingly are conventionally found as additives to the personal care products. To keep the number of additives within reasonable bounds with respect to any particular skin care product, it would be desirable to use herb extracts that provide not only one or more of the performance enhancing properties but also an antioxidant property, and, more particularly, it would be beneficial to find combinations of herb extracts that provide synergistic antioxidant effects. That is, it would be useful to provide formulations of different herb extracts that would function synergistically to increase the total antioxidant activity of the combined extracts in excess of their individual contributions.

SUMMARY OF THE INVENTION

In accordance with one embodiment, the present invention comprises mixtures of herb extracts which exert synergistic antioxidant effect and comprise the herb ginger and at least one other herb selected from the group consisting of honeysuckle and *sophora*.

In accordance with another embodiment, the invention comprises a skin care preparation comprising a base which is medicinally acceptable for dermal application and which contains an antioxidant effective mixture of the herb ginger and at least one other herb selected from the group consisting of honeysuckle and *sophora*. The invention also comprises a method for the preparations of such skin preparation.

In accordance with another embodiment, the invention comprises a method for caring for the skin comprising applying to the skin a composition comprising an admixture of a base and an antioxidant effective mixture of the herb ginger and at least one other herb selected from the group consisting of honeysuckle and *sophora*.

BRIEF DESCRIPTION OF THE DRAWINGS

FIG. 1 is an XY scatter chart depicting the synergistic and non-synergistic results from the use of various concentration ratios of ginger/honeysuckle extract mixtures.

FIG. 2 is an XY scatter chart depicting the synergistic and non-synergistic results from the use of various concentration ratios of ginger/*sophora* extract mixtures.

DETAILED DESCRIPTION OF THE INVENTION

This detailed description of various exemplary embodiments of the invention makes reference to exemplary compositions and methods. While these embodiments are described in sufficient detail to enable those skilled in the art to practice the invention, it should be understood that other embodiments may also be realized, and that logical and processing changes may be made without departing from the spirit and scope of the invention. Thus, the detailed description herein is present for the purposes of illustration only and not of limitation.

In the development of the present invention, it was discovered that certain mixtures of extracts of the herb ginger with extracts of other herbs such as honeysuckle and *sophora* provide a synergistic antioxidant effect when prepared within certain ranges of concentration ratios. The detailed description of this discovery with respect to each herb mixture (i.e., ginger/honeysuckle and ginger/*sophora*) will be taken up separately in the sections to follow:

Mixtures of Ginger and Honeysuckle

Ginger is an herb extract obtained from the rhizome of the perennial plant *Zingiher officinale*, which is indigenous to a number of Asian and Eurasian areas, including China, India, Indonesia, etc. It is mentioned throughout history not only as a candy and food ingredient but also as a natural remedy for a wide range of ailments, including use for anti-inflammatory effect. The ginger extracts used in the present study were obtained from two different sources. The first was a powder extract ordered through Nankai University in China from Sha anxi Flua Teng Biology Project Co. Ltd. The second was a liquid extract obtained on the market from Symrise GMBH & Co., KG., Holzminden, Germany under the name Actipone® Ginger. In the present specification and claims, the extract will be referred to either as "ginger" or as "ginger (powder)" or as "ginger (liquid)", as may be applicable.

Honeysuckle is an herb extract obtained from the dried flowers of the plant *Lonicera japonica*. It is mentioned throughout history not only as a candy and food ingredient but also as a natural remedy for a wide range of ailments, including use for anti-inflammatory, anti-irritant, and vasodilatory effect. The honeysuckle extracts used in the present study were obtained on the market from Symrise GMBH & Co., KG., Holzminden, Germany, under the name Actipone® Honeysuckle Flower. In the present specification and claims, the extract will be referred to either as "honeysuckle" or "honeysuckle flower."

In the development of the present invention, the measurement of antioxidant activity was made using the oxygen radical absorbance capacity (ORAC) assay described in the publication by Huang, D.; Ou, B.; Hampshe-Woodill, M.; Flanagan, J. A.; and Prior, R. I., entitled "High-throughput assay of oxygen radical absorbance capacity (ORAC) using a multichannel liquid handling system coupled with a microplate fluorescence reader in 96-well format", 2002 *J. Agric. Food Chem.*, 50, 4437-4444. In these measurements, for each herb extract, the fluorescence decay curves of sodium fluorescein ($Na_2Fl$) induced by 2,2 prime—Azobis(-amidopropane)dihydrochloride (AAPH) in the presence of Trolox standards was evaluated. The ORAC measurement was performed at 30° C. on a Synergy™ HT multi-detection microplate reader (Bio-Tek Instruments, Inc., Winooski, Vt.) with an excitation wavelength of 485±20 nm and emission wavelength of 530±20 nm. The plate reader was controlled by software KC4 3.4.

In these measurements, an $8.0 \times 10^{-5}$ mM fresh $Na_2Fl$ solution was made daily by diluting the stock solution in 75 mM phosphate buffer (pH 7.4). AAPH (0.414 g) was completely dissolved in 10 ml of 75 mM phosphate buffer (pH 7.4) to a final concentration of 150 mM and was kept in an ice bath. Trolox standard was prepared as follows: 0.0125 g of Trolox was dissolved in 10 ml MeOH solution to give a 0.5M stock solution. The stock solution was diluted with the same phosphate buffer to 50, 25, 12.5 and 6.25 µM, i.e. 12.5, 6.25, 3.13, and 1.56 µg/ml working solutions. These samples were used in each test as control. In each test, samples were freshly prepared by dissolving into 75 mM phosphate buffer (pH 7.4) to make stock solution and then diluting and the phosphate buffer solution was tested as blank.

In the course of the work leading to the present invention, mixtures of ginger and honeysuckle in a number of varying concentration ratios were tested for antioxidant effectiveness using the ORAC assay method. The fluorescence decay curves of $Na_2Fl$ induced by AAPH in the presence of Trolox standards for each herb extract and the combination of herb extracts were plotted after each test. Their area under the curve (A.U.C.) was calculated. The net A.U.C. was calculated as $A.U.C._{sample} - A.U.C._{blank}$. The net A. U. C. from the combination of herb extracts and the sum of net A. U. C. from each herb extract were listed in table and also plotted in diagram. The results of such testing for a first group of mixtures, using ginger and honeysuckle are set forth in the following Table 1-A:

TABLE 1-A

Ginger and Honeysuckle

| Ginger Conc. µg/ml | HoneyS Conc. µg/ml | A.U.C | Net A.U.C. | Sum of each herb | Net − Sum | (Net − Sum)/Sum * 100* % |
|---|---|---|---|---|---|---|
| 8.9 | 0 | 49 | 43.83 | | | |
| 6.23 | 0 | 36.87 | 31.7 | | | |
| 3.12 | 0 | 21 | 15.83 | | | |
| 1.56 | 0 | 13.76 | 8.59 | | | |
| 0.78 | 0 | 9.04 | 3.87 | | | |
| 0 | 27.26 | 45.67 | 40.5 | | | |
| 0 | 19.08 | 31.78 | 26.61 | | | |
| 0 | 9.54 | 24 | 18.83 | | | |
| 0 | 4.77 | 15.73 | 10.56 | | | |
| 0 | 2.39 | 11.41 | 6.24 | | | |
| 8.9 | 4.77 | 60.54 | 55.37 | 54.39 | 0.98 | 1.80 |
| 8.9 | 2.39 | 56.33 | 51.16 | 50.07 | 1.09 | 2.18 |
| 6.23 | 9.54 | 55.86 | 50.69 | 50.53 | 0.16 | 0.32 |
| 6.23 | 4.77 | 48.37 | 43.2 | 42.26 | 0.94 | 2.22 |
| 6.23 | 2.39 | 42.25 | 37.08 | 37.94 | −0.86 | −2.27 |
| 3.12 | 19.08 | 54.91 | 49.74 | 42.44 | 7.3 | 17.20 |
| 3.12 | 9.54 | 38.2 | 33.03 | 34.66 | −1.63 | −4.70 |
| 3.12 | 4.77 | 29.29 | 24.12 | 26.39 | −2.27 | −8.60 |
| 1.56 | 19.08 | 51.39 | 46.22 | 35.2 | 11.02 | 31.31 |
| 1.56 | 9.54 | 34.2 | 29.03 | 27.42 | 1.61 | 5.87 |
| 1.56 | 2.39 | 20.92 | 15.75 | 14.83 | 0.92 | 6.20 |
| 0.78 | 27.26 | 56.33 | 51.16 | 44.37 | 6.79 | 15.30 |
| 0.78 | 19.08 | 42.67 | 37.5 | 30.48 | 7.02 | 23.03 |
| 0.78 | 9.54 | 25.8 | 20.63 | 22.7 | −2.07 | −9.12 |
| 0.78 | 2.39 | 12.59 | 7.32 | 10.11 | −2.69 | −26.61 |
| Blank | | 5.17 | | | | |

It will be noted that, in the above Table 1-A, a positive percentage number in the (Net−Sum)/Sum*100 column indicates that the mixtures possesses synergistic effect, while a negative percentage number indicates non-synergistic effect.

To summarize the synergistic and non-synergistic findings in the above studies, the synergistic ratios are tabulated below in Table 1-B, and the non-synergistic ratios are set out below in Table 1-C:

TABLE 1-B

Synergistic Ginger/Honeysuckle Concentration ratios

| Ginger µg/ml | Honeysuckle µg/ml |
|---|---|
| 8.9 | 4.77 |
| 8.9 | 2.39 |
| 6.23 | 9.54 |
| 6.23 | 4.77 |
| 3.12 | 19.08 |
| 1.56 | 19.08 |
| 1.56 | 9.54 |
| 1.56 | 2.39 |
| 0.78 | 27.26 |
| 0.78 | 19.08 |

TABLE 1-C

Non-synergistic Ginger/Honeysuckle Concentration ratios

| Ginger µg/ml | Honeysuckle µg/ml |
|---|---|
| 6.23 | 2.39 |
| 3.12 | 9.54 |
| 3.12 | 4.77 |
| 0.78 | 9.54 |
| 0.78 | 2.39 |

The data of Tables 1-B and 1-C have been incorporated in an XY scatter chart which is presented in this application as FIG. 1. It will be noted that the concentration ratios found to be synergistic are located within the area marked A on the chart.

To summarize all of the foregoing, in the embodiment of the invention involving mixtures of sophora and honeysuckle, the concentration ratios which have been found to be synergistic are within the range of 0.5 µg/ml≦$C_{Ginger}$≦9.0 µg/ml, 2.0 µg/ml≦$C_{Honeysuckle}$≦27.0 µg/ml.

Mixtures of Ginger and Sophora

In the embodiment involving mixtures of ginger and sophora, ginger is the herb extract obtained from the rhizome of the perennial plant Zingiher officinale, which is described in more detail in the previous section. Sophora flower is the dried flower of the Japanese pagoda tree (Sophora japonica), which is native to Japan, China, Korea and other Eastern Asia countries It is described as having numerous medicinal uses, particularly in traditional Chinese medicine, including use as an anti-inflammatory agent. The sophora flower extracts used in the present study were obtained from Symrise GMBH & Co., KG., Holzminden, Germany, under the name Actipone® Sophora Flower. In the present specification and claims, the extract will be referred to either as "sophora" or as "sophora flower."

In the development of the ginger/sophora embodiment of the present invention, the measurement of antioxidant activity was made using the oxygen radical absorbance capacity (ORAC) assay, which is described in detail in the preceding section relating to the ginger/honeysuckle embodiment.

In the course of the work leading to the present invention, mixtures of ginger and sophora in a number of varying concentration ratios were tested for antioxidant effectiveness using the ORAC assay method to obtain net A.U.C. values, and the results of such testing for a first group of mixtures are set forth in the following Table 2-A:

TABLE 2-A

Ginger and Sophora

| Ginger Conc. µg/ml | Sophora Conc. µg/ml | A.U.C | Net A.U.C. | Sum of each herb | Net − Sum | (Net − Sum)/ Sum * 100* % |
|---|---|---|---|---|---|---|
| 8.9 | 0 | 48.06 | 42.89 | | | |
| 6.23 | 0 | 36.15 | 30.98 | | | |
| 3.12 | 0 | 13.58 | 8.41 | | | |
| 1.56 | 0 | 14.22 | 9.2 | | | |
| 0.78 | 0 | 9.56 | 4.39 | | | |
| 0 | 26.36 | 56.29 | 51.12 | | | |
| 0 | 18.45 | 38.62 | 33.45 | | | |
| 0 | 9.23 | 27.22 | 22.05 | | | |
| 0 | 4.61 | 16.74 | 11.57 | | | |
| 0 | 2.31 | 11.25 | 6.08 | | | |
| 8.9 | 9.23 | 68.86 | 63.69 | 64.94 | −1.25 | −1.92 |
| 8.9 | 2.31 | 56.78 | 51.661 | 48.97 | 2.64 | 5.39 |
| 6.23 | 18.45 | 72.69 | 67.52 | 64.43 | 3.09 | 4.80 |
| 6.23 | 4.61 | 49.22 | 44.05 | 42.55 | 1..5 | 3.53 |
| 6.23 | 2.31 | 43.57 | 38.4 | 37.06 | 1.34 | 3.62 |
| 3.12 | 26.36 | 70.66 | 65.49 | 67.57 | −2.08 | −3.08 |
| 3.12 | 18.45 | 60.39 | 55.22 | 49.9 | 5.32 | 10.66 |
| 3.12 | 4.61 | 31.02 | 25.85 | 28.02 | −2.17 | −7.74 |
| 1.56 | 26.36 | 68.98 | 63.81 | 59.53 | 4.28 | 7.19 |
| 1.56 | 9.23 | 38.85 | 33.68 | 30.46 | 3.22 | 10.57 |
| 1.56 | 2.31 | 20.92 | 15.75 | 14.49 | 1.26 | 8.70 |
| 0.78 | 26.36 | 63.04 | 56.87 | 55.51 | 2.36 | 5.25 |
| 0.78 | 18.45 | 52.3 | 47.13 | 37.84 | 9.29 | 24.55 |
| 0.78 | 9.23 | 30.15 | 24.98 | 26.44 | −1.46 | −5.52 |
| 0.78 | 2.31 | 14.94 | 9.77 | 10.47 | −0.7 | −6.69 |
| Blank | | 5.02 | | | | |

It will be noted that, in the above Table 2-A, a positive percentage number in the (Net−Sum)/Sum*100 column indicates that the mixtures possesses synergistic effect, while a negative percentage number indicates non-synergistic effect.

To summarize the synergistic and non-synergistic findings in the above two studies relating to mixtures of ginger and sophora, the synergistic ratios are tabulated below in Table 2-B, and the non-synergistic ratios are set out below in Table 2-C:

TABLE 2-B

Synergistic Ginger/Sophora Concentration ratios

| Ginger µg/ml | Sophora µg/ml |
|---|---|
| 8.9 | 2.31 |
| 6.23 | 18.45 |
| 6.23 | 4.61 |
| 6.23 | 2.31 |
| 3.12 | 18.45 |
| 1.56 | 26.36 |
| 1.56 | 9.23 |
| 1.56 | 2.31 |
| 0.78 | 26.36 |
| 0.78 | 18.45 |

TABLE 2-C

Non-synergistic Ginger/Sophora Concentration ratios

| Ginger µg/ml | Sophora µg/ml |
|---|---|
| 8.9 | 9.23 |
| 3.12 | 26.36 |
| 3.12 | 4.61 |
| 0.78 | 9.23 |
| 0.78 | 2.31 |

The data of Tables 2-B and 2-C have been incorporated in an XY scatter chart which is presented in this application as FIG. 2, relating to mixtures of ginger and sophora extracts. It will be noted that the concentration ratios found to be synergistic are located within the area marked A on the chart.

To summarize the above data for the embodiment of the invention involving mixtures of ginger and sophora extracts, the concentration ratios which have been found to be synergistic are within the range of 0.5 µg/ml≦$C_{Ginger}$≦9.0 µg/ml, 2.0 µg/ml≦$C_{Sophora}$≦27.0 µg/ml.

In the practice of the invention, the plant extract combinations mentioned above may be included in any suitable skin care bases medicinally acceptable for dermal application, including various base formulations such as liquids, creams, gels; foams, lotions, body washes, liquid hand soaps, shampoos, antiperspirants, deodorants, and the like. Such base formulations conventionally contain known skin care ingredients, such as found in "CFTA Cosmetic Ingredient Handbook," J. M. Nikitakis, ed., The Cosmetic, Toiletry and Fragrance Association, Inc., Washington, D.C. (1988), incorporated herein by reference. Such ingredients include, but not by way of limitation, numerous enhancing elements, such as alcohols, oleaginous substances, surfactants, preservatives, emollients, perfumes, colorants, humectants, thickening agents, skin care agents, water-soluble polymers, chelating agents, pH adjusting agents, foaming agents, antimicrobial agents, vitamins, and the like.

Examples of the above-mentioned surfactants include, but are not limited to, lauryl sulfates, octyl sulfates, 2-ethylhexyl sulfates, lauramine oxides, decyl sulfates, tridecyl sulfates, cocoates, lauryl sulfosuccinates, lauryl sarcosinates, lauryl ether sulfates (1 and 2 moles ethylene oxide), myristamine oxide, ricinoleates, cetyl sulfates, alkyl glucosides, and similar surfactants.

Examples of the above preservatives include benzoic acid salts, salicylic acid salts, sorbic acid salts, dehydroacetic acid salts, parahydroxybenzoic acid esters, benzalkonlium chloride, 2,4,4'-trichloro-2'-hydroxydiphenyl ether, 3,4,4'-trichlorocarbanilide, hinokitiol, resorcinol, and ethanol.

Examples of humectants include glycerin, sodium pyrrolidone carboxylate, and the like. Examples of foam stabilizers include cetyl alcohol, cetearyl alcohol, stearic acid, and the like. Examples of skin care agents include guar gum, hydroxyethylcellulose, hydroxypropylmethylcellulose, polyethylene glycol, hydrolyzed wheat protein, polyoxyethylene stearyl ether, and the like.

The actual formulation of the skin care consumer products incorporating the plant extract combinations of the present invention is through standard methods of manufacturing. All the liquid formulations are easily made in batch mixtures, with addition of water usually first, such that the liquid is above the mixing impeller within the tank. Then the specialty chemicals, such as the surfactants are added, followed by the dyes, preservatives, plant extract combinations, etc. The methods of manufacture are well known.

The following examples are presented for the purpose of further illustrating various formulations of skin care bases incorporating the plant extracts of the present invention and are not to be taken as limiting in any regard.

Example 1

Liquid Hand Soap Formulation with Ginger/Honeysuckle Herb Extracts

| Ingredient | Active Wt (%) |
| --- | --- |
| Water (Purified) | 75.280 |
| Sodium Xylenne Sulfonate | 15.000 |
| Dipropylenen Glycol | 5.000 |
| Ammoniun Lauryl Sulfate | 2.500 |
| Triclosan | 0.975 |
| Cocamidopropyl Betaine | 0.750 |
| Fragrance | 0.200 |
| Sodium Phosphate | 0.129 |
| Citric Acid | 0.066 |
| Ginger extract | 0.020 |
| Honeysuckle flower extract | 0.080 |

Example 2

Body Wash Formulation with Ginger/Honeysuckle Herb Extracts

| Ingredient | Active Wt (%) |
| --- | --- |
| Water (D.I) | 84.462 |
| Polyquaternium-10 | 0.200 |
| Tetrasodium EDTA | 0.010 |
| Glycerin | 1.000 |
| PEG-8 | 3.000 |
| Cocamidopropyl Betaine | 5.200 |
| Sodium Laureth Sulfate | 5.500 |
| Cocamidopropyl PG-Dimonium Chloride | 0.123 |
| Tetrasodium EDTA | 0.010 |
| Isostearamidopropyl Morpholine Lactate | 0.100 |
| Citric Acid, Anhydrous | 0.040 |
| Hydantoin | 0.055 |
| Ginger extract | 0.020 |
| Honeysuckle flower extract | 0.080 |
| Fragrance | 0.200 |
| Sodium Chloride | 0.001 |

Example 3

Roll-On Antiperspirant Formulation with Ginger/Honeysuckle Herb Extracts

| Ingredient | Active Wt (%) |
| --- | --- |
| Cyclomethicone DC 245 | 78.100 |
| Quaternium-18 Hectorite | 4.500 |
| Propylene Carbonate | 1.000 |
| Summit AAZG-3108 | 16.300 |
| Ginger extract | 0.020 |
| Honeysuckle flower extract | 0.080 |

Example 4

Lotion Formulation with Ginger/Honeysuckle Herb Extracts

| Ingredient | Active Wt (%) |
| --- | --- |
| Water (D.I) | 84.630 |
| Glycerin | 5.300 |
| Stearic Acid | 2.000 |
| Octyl Palmitate | 1.750 |
| Petrolatum | 1.200 |
| Glyceryl Stearate | 1.200 |
| Ethylene Glycol Monostearate | 1.200 |
| Cetyl Alcohol | 0.750 |
| Dimethicone | 0.500 |
| Fragrance | 0.500 |
| Propylene Glycol Dicaprylate/Dicaprate | 0.300 |
| Methylparaben | 0.200 |
| Carbomer | 0.150 |
| Ginger extract | 0.020 |
| Honeysuckle flower extract | 0.080 |
| Propylparaben | 0.100 |
| Sodium Hydroxide | 0.100 |
| Tetrasodium EDTA | 0.020 |

Example 5

Liquid Hand Soap Formulation with Ginger/*Sophora* Herb Extracts

| Ingredient | Active Wt (%) |
| --- | --- |
| Water (Purified) | 75.280 |
| Sodium Xylenne Sulfonate | 15.000 |
| Dipropylenen Glycol | 5.000 |
| Ammoniun Lauryl Sulfate | 2.500 |
| Triclosan | 0.975 |
| Cocamidopropyl Betaine | 0.750 |
| Fragrance | 0.200 |
| Sodium Phosphate | 0.129 |
| Citric Acid | 0.066 |
| Ginger extract | 0.020 |
| Sophora extract | 0.080 |

Example 6

Body Wash Formulation with Ginger/*Sophora* Herb Extracts

| Ingredient | Active Wt (%) |
| --- | --- |
| Water (D.I) | 84.462 |
| Polyquaternium-10 | 0.200 |
| Tetrasodium EDTA | 0.010 |
| Glycerin | 1.000 |
| PEG-8 | 3.000 |
| Cocamidopropyl Betaine | 5.200 |
| Sodium Laureth Sulfate | 5.500 |
| Cocamidopropyl PG-Dimonium Chloride | 0.123 |
| Tetrasodium EDTA | 0.010 |
| Isostearamidopropyl Morpholine Lactate | 0.100 |
| Citric Acid, Anhydrous | 0.040 |
| Hydantoin | 0.055 |
| Ginger extract | 0.020 |
| Sophora extract | 0.080 |
| Fragrance | 0.200 |
| Sodium Chloride | 0.001 |

Example 7

Roll-On Antiperspirant Formulation with Ginger/*Sophora* Herb Extracts

| Ingredient | Active Wt (%) |
| --- | --- |
| Cyclomethicone DC 245 | 78.100 |
| Quaternium-18 Hectorite | 4.500 |
| Propylene Carbonate | 1.000 |
| Summit AAZG-3108 | 16.300 |
| Ginger extract | 0.020 |
| Sophora extract | 0.080 |

Example 8

Lotion Formulation with Ginger/*Sophora* Herb Extracts

| Ingredient | Active Wt (%) |
| --- | --- |
| Water (D.I) | 84.630 |
| Glycerin | 5.300 |
| Stearic Acid | 2.000 |
| Octyl Palmitate | 1.750 |
| Petrolatum | 1.200 |
| Glyceryl Stearate | 1.200 |
| Ethylene Glycol Monostearate | 1.200 |
| Cetyl Alcohol | 0.750 |
| Dimethicone | 0.500 |
| Fragrance | 0.500 |
| Propylene Glycol Dicaprylate/Dicaprate | 0.300 |
| Methylparaben | 0.200 |
| Carbomer | 0.150 |
| Ginger extract | 0.020 |
| Sophora extract | 0.080 |
| Propylparaben | 0.100 |
| Sodium Hydroxide | 0.100 |
| Tetrasodium EDTA | 0.020 |

While numerous exemplary embodiments of the invention have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention set forth in the appended claims and their legal equivalents.

We claim:

1. A skin care composition comprising a mixture of ginger and honeysuckle extracts which exerts synergistic antioxidant effect and in which the ginger and honeysuckle are within the concentration range of $0.5\ \mu g/ml \leqq C_{Ginger} \leqq 9.0\ \mu g/ml$, $2.0\ \mu g/ml \leqq C_{Honeysuckle} \leqq 27.0\ \mu g/ml$.

2. A skin care composition of herb extracts which provides synergistic antioxidant effects, comprising a mixture of ginger and honeysuckle extracts having a concentration falling approximately within the area marked A in the chart shown in FIG. 1 hereof.

3. A skin care preparation comprising a base medicinally acceptable for dermal application having mixed therein the composition of herb extracts as defined in claim 1.

4. A skin care preparation comprising a base medicinally acceptable for dermal application having mixed therein the composition of herb extracts as defined in claim 2.

5. A method for making a skin care preparation, the method comprising admixing a base and the synergistic antioxidant composition as defined in claim 1.

6. A method for making a skin care preparation, the method comprising admixing a base and the synergistic antioxidant composition as defined in claim 2.

7. A method for caring for the skin comprising applying to the skin a skin care preparation as defined in claim 3.

8. A method for caring for the skin comprising applying to the skin a skin care preparation as defined in claim 4.

* * * * *